US005739354A

United States Patent [19]

Rudisill

[11] Patent Number: 5,739,354
[45] Date of Patent: Apr. 14, 1998

[54] PROCESS FOR THE PREPARATION OF N-METHYL-D-PHENYLALANYL-N-[1-[3-[(AMINOIMINOMETHYL)AMINO]PROPYL]-3,3-DIFLUORO-2-OXOHEXYL]-L-PROLINAMIDE

[75] Inventor: Duane E. Rudisill, West Chester, Ohio

[73] Assignee: Hoechst Marion Roussel, Inc., Cincinnati, Ohio

[21] Appl. No.: 786,997

[22] Filed: Jan. 23, 1997

Related U.S. Application Data

[60] Provisional application No. 60/052,854 Mar. 26, 1996
[51] Int. Cl.$^6$ .................. C07D 207/08; C07C 215/06
[52] U.S. Cl. ........................................ 548/537; 564/503
[58] Field of Search ........................... 548/537; 564/503

[56] References Cited

U.S. PATENT DOCUMENTS

| | | | |
|---|---|---|---|
| 4,061,625 | 12/1977 | Af Ekenstam et al. | 260/112.5 R |
| 4,216,142 | 8/1980 | Ali | 260/112.5 R |
| 4,217,269 | 8/1980 | Cole | 260/112.5 R |
| 4,247,454 | 1/1981 | Af Ekenstam et al. | 260/112.5 R |
| 4,275,153 | 6/1981 | Gargiulo et al. | 435/13 |
| 4,318,904 | 3/1982 | Shaw et al. | 424/177 |
| 4,399,065 | 8/1983 | Bajusz et al. | 260/112.5 R |
| 4,450,105 | 5/1984 | Nagasawa et al. | 260/112.5 R |
| 4,478,745 | 10/1984 | Bajusz et al. | 260/112.5 R |
| 4,607,047 | 8/1986 | Debay | 514/428 |
| 4,643,991 | 2/1987 | Digenis et al. | 514/18 |
| 4,703,036 | 10/1987 | Bajusz et al. | 514/18 |
| 4,720,484 | 1/1988 | Vincent et al. | 514/18 |
| 4,762,821 | 8/1988 | Nestor | 514/19 |
| 4,816,562 | 3/1989 | Verdini et al. | 530/323 |
| 4,826,814 | 5/1989 | Sawayama et al. | 514/18 |
| 4,847,401 | 7/1989 | Gerhart et al. | 558/378 |
| 4,880,780 | 11/1989 | Trainor et al. | 514/18 |
| 4,929,602 | 5/1990 | Harker et al. | 514/18 |
| 4,980,349 | 12/1990 | Roger et al. | 574/231.8 |
| 5,053,392 | 10/1991 | Klein et al. | 514/18 |
| 5,391,705 | 2/1995 | Neises et al. | 530/331 |
| 5,498,779 | 3/1996 | Neises et al. | 514/18 |

FOREIGN PATENT DOCUMENTS

| | | |
|---|---|---|
| 0195212 | 8/1986 | European Pat. Off. . |
| 0410411 | 1/1991 | European Pat. Off. . |
| 0503203 | 3/1991 | European Pat. Off. . |
| 0498508 | 2/1992 | European Pat. Off. . |
| 2287027 | 9/1995 | United Kingdom . |
| 9425051 | 4/1994 | WIPO . |

OTHER PUBLICATIONS

Pitzele, Barrett S., J. Med. Chem, 1994, vol. 37, pp. 888–896.
Shuman, Robert T., J. Med. Chem 1993, vol. 36, pp. 314–319.

Chem Absts, vol 110, p. 709, 1989, No. 76058; Angliker, "Synthesis and properties of peptidyl derivatives of arginylfluoromethames" (Biochemical Journal, vol 256, No. 2, pp. 481–486.

Angliker et al., Biochem.J. 256(2), 481–6 (1988).

Gelb et al., "Fluoro Ketone inhibitors of Hydrolytic Enzymes," Biochemistry, vol. 24, No. 8, pp. 1813–1817, 1985.

Sham et al., "Highly potent and specific inhibitors of human renin", FEBS Letters, vol. 220, No. 2, pp. 299–301, 1987.

Chem Absts, vol. 107, 1987, No. 40336Y, p. 758; Stueber, M: Oligopeptidylargininol derivatives and their homologs, their use as antithrombics and agents containing them.

Shuman et al., Proceedings of the 12th American Peptide Symposium, pp. 801–802, (1991).

Kolb et al, Tetrahedron Lettes vol. 27, No. 14, pp. 1579–1582 (1986).

Kolb et al, Tetrahedron Lettes vol. 27, No. 37, pp. 4437–4440 (1986).

Kolb, M., et al, Liebigs Ann. Chem., pp. 1–6, (1990).

Peet N. P., et al, J. Med. Chem. 33, pp. 394–407, (1990).

Neises, B., et al Journal of the International Society on Thrombosis and Haemostasis, Abstracts p. 1290, 1991.

Neises, B., et al Journal of the International Society on Thrombosis and Haemostatis, Abstracts p. 1290, 1992.

Neises et al., Bioorganic & Medicinal Chemistry, vol. 3, No. 8, pp. 1049–1061, 1995, Synthesis and Comparison of Tripeptidylfluoroalkane Thrombin Inhibitors.

Begue et al, Tetrahedron, vol. 47, No. 20/21, pp. 3207–3258, Jan. 21, 1991.

Broersma et al., Thrombosis and Haemostasis 69, 666 (1993).

Derwent Abstract, EP 0 185 390, Jun. 25, 1986.

Derwent Abstract, EP 0 192 135, Feb. 18, 1985.

Hoffmann, et al, N'–Formyl–L–Lysine in Peptide Synthesis, Jul. 20, 1960, Studies in Polypeptides. XVI. The Preparation of N'–Formyl–L–lysine and its Application to the Synthesis of Peptides, pp. 3727–3732.

Narayanan et al, J. Med. Chem. 1994, 37, 885–887, SDynthesis of L–Thiocitrulline, L–Homothiocitrulline, and S–Methyl–L–thiocitrulline: A New Class of Potential Nitric Oxide Synthase Inhibitors.

*Primary Examiner*—Joseph McKane
*Attorney, Agent, or Firm*—T. Helen Payne

[57] ABSTRACT

The present invention relates to a novel process for preparing preparing N-methyl-D-phenylalanyl-N-[1-[3-[(aminoiminomethyl)amino]propyl]-3,3-difluoro-2-oxohexyl]-L-prolinamide or a pharmaceutically acceptable salt thereof and to a key intermediate by directly guanylating Dakin-West intermediates.

20 Claims, No Drawings

PROCESS FOR THE PREPARATION OF N-METHYL-D-PHENYLALANYL-N-[1-[3-[(AMINOIMINOMETHYL)AMINO]PROPYL]-3,3-DIFLUORO-2-OXOHEXYL]-L-PROLINAMIDE

This application claims the priority of U.S. application Ser. No. 08/624,721 (converted to a provisional application on Jan. 13, 1997, Ser. No. 60/052,854) filing date Mar. 26, 1996.

FIELD OF THE INVENTION

The present invention relates to a novel process for preparing N-methyl-D-phenylalanyl-N-[1-[3-[(aminoiminomethyl)amino]propyl]-3,3-difluoro-2-oxohexyl]-L-prolinamide and to pharmaceutically acceptable salts thereof.

BACKGROUND OF THE INVENTION

N-methyl-D-phenylalanyl-N-[1-[3-[(aminoiminomethyl)amino]propyl]-3,3-difluoro-2-oxohexyl]-L-prolinamide dihydrochloride monohydrate (also known as "MDL 75,579DA") is described in U.S. Pat. No. 5,391,705 and is an inhibitor of both thrombin and tryptase. The compound is useful in an end-use application as an anticoagulant and for treating thrombophlebitis, coronary thrombosis and in the treatment of asthma. The biochemical and pharmacological effects of N-methyl-D-phenylalanyl-N-[1-[3-[(aminoiminomethyl)amino]propyl]-3,3-difluoro-2-oxohexyl]-L-prolinamide dihydrochloride monohydrate are described in R. J. Broersma et al., *Thrombosis and Haemostasis* 69, 666 (1993) and B. Neises et al., *Bioorg. Med. Chem.* 3, 1049–1061 (1995).

U.S. Pat. No. 5,391,705 discloses the convergent preparation of N-methyl-D-phenylalanyl-N-[1-[3-[(aminoiminomethyl)amino]propyl]-3,3-difluoro-2-oxohexyl]-L-prolinamide dihydrochloride monohydrate from a nitro intermediate. For example, 4-amino-1-nitrobutane hydrochloride is directly guanylated with bis-Boc-S-methylisothiourea. The guanylated product is then coupled to 2,2-difluoropentene-1-al, ethyl hemiacetal, to form a 5-hydroxy-6-nitro intermediate which is reduced by catalytic hydrogenation to form a 5-hydroxy-6-amino intermediate. The 5-hydroxy-6-amino intermediate is then coupled to a N-Boc-N-methyl-D-Phe-L-Pro dipeptide intermediate and the coupled peptide is oxidized using typical oxidizing procedures such as the Swern oxidation, to form N-methyl-D-phenylalanyl-N-[1-[3-[(aminoiminomethyl)amino]propyl]-3,3-difluoro-2-oxohexyl]-L-prolinamide dihydrochloride monohydrate.

Alternatively, B. Neises et al., *Bioorg. Med. Chem.* 3, 1049–1061 (1995) discloses, and U.S. Pat. No. 5,391,705 suggests, using a modified Dakin-West reaction of 2-phenyl-[4-(3-benzyloxycarbonylaminopropyl)]-5-(4H)-oxazolane and the anhydrides or acyl halides of 2,2-difluoro-4-pentenoic acid to yield 9,6-diamino-5-hydroxy-4,4-difluorononane, bis hydrochloride. The bis hydrochloride is then guanylated using a three-step guanylation procedure which involves trifluoroacetic acid anhydride ("TFAA") protection of the internal amine, guanylation of the terminal amine and removal of the TFA-protecting group. The resulting 5-hydroxy-6-amino intermediate is then coupled to a N-Boc-N-methyl-D-Phe-L-Pro dipeptide intermediate and the coupled peptide is oxidized using typical oxidizing procedures such as the Swern oxidation, to form N-methyl-D-phenylalanyl-N-[1-[3-[(aminoiminomethyl)amino]propyl]-3,3-difluoro-2-oxohexyl]-L-prolinamide dihydrochloride monohydrate.

These methods, however, possess some disadvantages. With regard to the process utilizing an appropriate nitro intermediate, there exist difficulties in the preparation of the 4-guanyl-1-nitrobutane intermediate. For example, when sodium nitrite is added to bromobutylphthalimide, the starting material, high yields of nitrobutylphthalimide, the desired intermediate, are difficult to obtain because of nitrite formation. Also, the nitrite must be hydrolyzed and separated from the desired nitrobutylphthalimide. Additionally, excess hydrazine is needed to remove the phthalimido group. In order to remove the toxic hydrazine, an excess of the expensive reagent $Boc_2O$ is required to be added to the crude mixture and the corresponding carbamates must be removed by chromatography. Besides the difficulty in preparing the appropriate 4-guanyl-1-nitrobutane intermediate, acceptable product purity (>97%) has been difficult to obtain and numerous chromatographic purifications are required in the synthesis.

As for the Dakin-West route, the three-step guanylation process gave poor yields of the final product, MDL 75,579DA, of only about 15%, starting from the N-9-[1-[3-[bis[(1,1-dimethylethoxy)carbonyl]amino]methylene]amino-6-amino-5-hydroxy-4,4-difluorononane intermediate. Furthermore, using the Dakin-West, three-step guanylation route, a product purity of only about 92% was obtained. However, because of concerns of guanylating the unprotected internal amine (i.e., the 6-amino group), the art taught and suggested that protection of the internal amine was necessary for selective guanylation of 9,6-diamino-5-hydroxy-4,4-difluorononane, bis-hydrochloride; K. Hofmann et al., *J. Am. Chem. Soc.* 82, 3727–3732 (1960); K. Narayanan and O. Griffith, *J. Med. Chem.* 37, 885–887 (1994); F. Weygard and R. Geiger, *Berichte der Deutschen Chemishen Gellellschaft*, 89, 647 (1956).

It is an object of the present invention to provide novel methods for the preparation of N-methyl-D-phenylalanyl-N-[1-[3-[(aminoiminomethyl)amino]propyl]-3,3-difluoro-2-oxohexyl]-L-prolinamide or a pharmaceutically acceptable salt thereof that allow for the selective, one-step guanylation of desirable Dakin-West intermediates, as opposed to the difficult to make 4-guanyl-1-nitrobutane intermediate.

It is a further object of the present invention to provide novel methods for the economical preparation of N-methyl-D-phenylalanyl-N-[1-[3-[(aminoiminomethyl)amino]propyl]-3,3-difluoro-2-oxohexyl]-L-prolinamide or a pharmaceutically acceptable salt thereof which can be carried out using fewer steps and fewer purifications than are disclosed previously in the art.

It is also a further object of the present invention to provide novel methods for the preparation of N-9-[1-[3-[bis (K$_1$-protected)amino]methylene]amino]-6-amino-5-hydroxy-4,4-difluorononane, wherein K$_1$ is an N-protecting group suitable for protecting the nitrogens of guanyl moieties, a desirable intermediate useful in the preparation of N-methyl-D-phenylalanyl-N-[1-[3-[(aminoiminomethyl)amino]propyl]-3,3-difluoro-2-oxohexyl]-L-prolinamide or a pharmaceutically acceptable salt thereof.

These and other objects disclosed herein are attained by the following claimed invention.

SUMMARY OF THE INVENTION

The present invention relates to a novel process for preparing N-methyl-D-phenylalanyl-N-[1-[3-[

(aminoiminomethyl)amino]propyl]-3,3-difluoro-2-oxohexyl]-L-prolinamide or a pharmaceutically acceptable salt thereof comprising the steps of:

(a) reacting 9,6-diamino-5-hydroxy-4,4-difluorononane, or a pharmaceutically acceptable salt thereof, with an appropriate guanylating agent to provide N-9-[1-[3-[bis($K_1$-protected)amino]methylene]amino]-6-amino-5-hydroxy-4,4-difluorononane, wherein $K_1$ is an N-protecting group suitable for protecting the nitrogens of guanyl moieties;

(b) coupling the N-9-[1-[3-[bis($K_1$-protected)amino]-methylene]amino]-6-amino-5-hydroxy-4,4-difluorononane with N-$K_2$-protected-N-methyl-D-phenylalanyl-L-prolinamide to provide N-$K_2$-protected-N-methyl-D-phenylalanyl-N-[1-[3-[[bis[($K_1$-protected)amino]methylene]amino]propyl]-3,3-difluoro-2-hydroxyhexyl]-L-prolinamide, wherein $K_2$ is an N-protecting group;

(c) reacting N-$K_2$-protected-N-methyl-D-phenylalanyl-N-[1-[3-[[bis[($K_1$-protected)amino]methylene]amino]propyl]-3,3-difluoro-2-hydroxyhexyl]-L-prolinamide with an appropriate oxidizing agent to provide N-$K_2$-protected-N-methyl-D-phenylalanyl-N-[1-[3-[[bis[($K_1$-protected)amino]methylene]-amino]propyl]-3,3-difluoro-2-oxohexyl]-L-prolinamide; and (d) deprotecting N-$K_2$-protected-N-methyl-D-phenylalanyl-N-[1-[3-[[bis[($K_1$-protected)amino]methylene]amino]propyl]-3,3-difluoro-2-oxohexyl]-L-prolinamide with a suitable deprotecting agent to provide N-methyl-D-phenylalanyl-N-[1-[3-[(aminoiminomethyl)amino]propyl]-3,3-difluoro-2-oxohexyl]-L-prolinamide or a pharmaceutically acceptable salt thereof.

The invention further provides a process for preparing N-9-[1-[3-[bis($K_1$-protected)amino]methylene]amino]-6-amino-5-hydroxy-4,4-difluorononane comprising reacting 9,6-diamino-5-hydroxy-4,4-difluorononane, or a pharmaceutically acceptable salt thereof, with an appropriate guanylating agent to give N-9-[1-[3-[bis($K_1$-protected)amino]methylene]-amino]-6-amino-5-hydroxy-4,4-difluorononane, wherein $K_1$ is an N-protecting group suitable for protecting the nitrogens of guanyl moieties.

DETAILED DESCRIPTION OF THE INVENTION

As used in this application:

a) the designation "⁓" refers to a bond for which the stereochemistry is not designated.

b) the designation "◂━" refers to a bond that protrudes forward out of the plane of the page.

c) the designation "⸺" refers to a bond that protrudes backward out of the plane of the page.

d) the term "pharmaceutically acceptable salt" refers to acid addition salts.

The expression "pharmaceutically acceptable acid addition salts" is intended to apply to any non-toxic organic or inorganic acid addition salt of N-methyl-D-phenylalanyl-N-[1-[3-[(aminoimino-methyl)amino]propyl]-3,3-difluoro-2-oxohexyl]-L-prolinamide or intermediates thereof. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, trifluoroacetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Such salts can exist in either the hydrated or substantially anhydrous form.

Stereoisomers is a general term for all isomers that differ only in the orientation of their atoms in space. It includes isomers of compounds with more than one chiral center that are not mirror images of one another (diastereomers or diastereoisomers). The term "enantiomer" refers to two stereoisomers that are non superimposable mirror images of one another. The term "chiral center" refers to a carbon atom to which four different groups are attached. The nomenclature L/D or R/S is used as described in IUPAC-IUB Joint Commission on Biochemical Nomenclature, *Eur. J. Biochem.* 138, 9–37 (1984). A chiral material may either contain an equal amount of the R and S isomers (or L and D isomers) in which case it is called "racemic" or "a racemate" or it may not contain equal amounts of R and S (or L and D isomers) in which case it is called "optically active" or "nonracemic".

The term "N-protecting group suitable for protecting the nitrogens of guanyl moieties" is meant to include tert-butyloxycarbonyl (Boc), carbobenzyloxy (Cbz), tert-butyldimethylsilyl (TBDMS), tert-butyldiphenylsilyl (TBDPS) and the like.

The term "N-protecting group" is meant to include any N-protecting group suitable for use in peptide synthethis as described in Greene, "Protective Groups in Organic Chemistry", Chapter 7, John Wiley & Sons, New York (1981). Illustrative examples include, but are not limited to, tert-butyloxycarbonyl (Boc), carbobenzyloxy (Cbz), tert-butyldimethylsilyl (TBDMS), tert-butyldiphenylsilyl (TBDPS) and the like.

As used herein the term "amino acid" is meant to include the naturally occurring amino acids which are translated from the genetic code and comprise the building blocks of proteins. The term amino acid also includes, unless specifically stated otherwise, both (L)- and (D)- amino acids, chemically modified amino acids such as amino acid analogs, and naturally occurring amino acids which are not usually incorporated into proteins. Abbreviations of amino acid analogs included within the scope of the specification, as well as the amino and carboxy protecting groups are set forth in Table 1.

TABLE 1

| Amino Acid or Protecting Group | Symbol |
|---|---|
| Arginine | Arg |
| Phenylalanine | Phe |
| Ornithine | Orn |
| Proline | Pro |
| tert-butyloxycarbonyl | Boc |
| carbobenzyloxy | Cbz |
| acetyl | Ac |
| succinyl | Suc |
| phenylacetamidomethyl | PAM |

A general synthetic procedure for preparing N-methyl-D-phenylalanyl-N-[1-[3-[(aminoiminomethyl)amino]propyl]-3,3-difluoro-2-oxohexyl]-L-prolinamide is set forth in Scheme A. In Scheme A, starting materials and reagents unless indicated elsewhere in this application are well known and appreciated by one of ordinary skill in the art.

SCHEME A

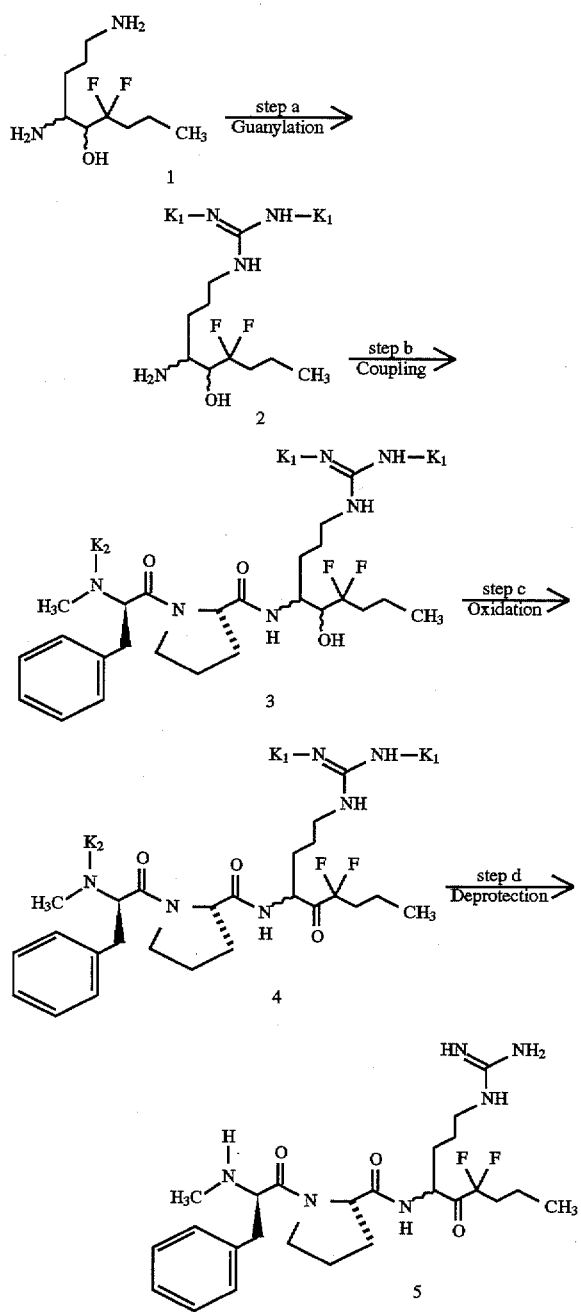

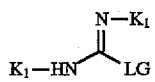

1a wherein $K_1$ refers to an N-protecting group suitable for protecting the nitrogens of guanyl moieties, including tert-butyloxycarbonyl (Boc), carbobenzyloxy (Cbz), tert-butyldimethylsilyl (TBDMS), tert-butyldiphenylsilyl (TBDPS) and the like, with tert-butyloxycarbonyl being preferred. The substituent LG refers to a suitable leaving group moiety and includes —S—CH$_3$, 1-pyrazole and the like. Appropriate guanylating agents include, but are not limited to, bis-Boc-amidinopyrazole, bis-Boc-S-methylisothiourea, bis-Cbz-amidinopyrazole, and the like, with bis-Boc-amidinopyrazole being preferred. The reaction is carried out in the presence of a suitable base. A suitable base may be utilized to neutralize a salt of the internal amine of 9,6-diamino-5-hydroxy-4,4-difluorononane, or a pharmaceutically acceptable salt thereof, 1, or may be utilized to neutralize the acid liberated when the appropriate guanylating agent, such as bis-Boc-amidinopyrazole, produces acid during the course of the reaction. Suitable bases include, but are not limited to, triethylamine, isopropyldiethylamine, N-methyl-morpholine, pyridine, sodium bicarbonate and sodium carbonate. The reaction is carried out in a suitable solvent, such as dichloromethane, dimethylformamide, tetrahydrofuran or tetrahydrofuran/water mixtures. In order to minimize the chance of guanylating the internal amine of 9,6-diamino-5-hydroxy-4,4-difluorononane, or a pharmaceutically acceptable salt thereof, 1, the guanylating agent is added in a ratio of from about 0.9 to about 1.2 molar equivalents, with from about 0.95 to 1.05 molar equivalents being preferred, for every 1.0 molar equivalent of 9,6-diamino-5-hydroxy-4,4-difluorononane, or a pharmaceutically acceptable salt thereof, 1. The reaction is carried out at a temperature of from about −30° C. to about 20° C., with −15° C. to 5° C. being preferred with −5° C. to 0° C. being most preferred. N-9-[1-[3-[bis($K_1$-protected)amino]methylene]-amino]-6-amino-5-hydroxy-4,4-difluorononane 2 may be isolated from the reaction zone by extraction and evaporation, as is well known in the art. N-9-[1-[3-[bis($K_1$-protected)amino]methylene]amino]-6-amino-5-hydroxy-4,4-difluorononane 2 optionally may be purified by techniques well known in the art, such as chromatography and recrystallization.

In Scheme A, step a, 9,6-diamino-5-hydroxy-4,4-difluorononane, or a pharmaceutically acceptable salt thereof, 1 is reacted with an appropriate guanylating agent to form N-9-[1-[3-[bis($K_1$-protected)amino]methylene]amino]-6-amino-5-hydroxy-4,4-difluorononane 2.

For example, 9,6-diamino-5-hydroxy-4,4-difluorononane, or a pharmaceutically acceptable salt thereof, 1 is contacted with an appropriate guanylating agent. Appropriate guanylating agents are well known in the art and are signified by structure 1a below:

In Scheme A, step b, N-9-[1-[3-[bis($K_1$-protected)-amino]methylene]amino]-6-amino-5-hydroxy-4,4-difluorononane 2 is coupled with N-$K_2$-protected-N-methyl-D-phenylalanyl-L-prolinamide ($K_2$-N-methyl-D-Phe-L-Pro) to provide N-$K_2$-protected-N-methyl-D-phenylalanyl-N-[1-[3-[[bis[($K_1$-protected)amino]methylene]amino]propyl]-3,3-difluoro-2-hydroxyhexyl]-L-prolinamide 3.

For example, N-9-[1-[3-[bis($K_1$-protected)amino]-methylene]amino]-6-amino-5-hydroxy-4,4-difluorononane 2 is coupled with $K_2$-N-methyl-D-Phe-L-Pro, wherein $K_2$ is an N-protecting group, preferably tert-butyloxycarbonyl (Boc) being preferred, using standard solution phase peptide synthesis techniques well known and appreciated by those skilled in the art. Standard solution phase peptide synthesis techniques include procedures such as the azide method, mixed carbonic-carboxylic acid anhydride (isobutyl chloroformate) method, carbodiimide (dicyclohexylcarbodiimide, diisopropylcarbodiimide, or water-soluble carbodiimide) method, active ester (p-nitrophenyl ester, N-hydroxy-succinic imido ester) method, Woodward reagent K method, carbonyldiimidazole method, phosphorus reagents such as BOP-Cl, or oxidation-reduction methods. The carbodiimide coupling is preferred. Some of these methods (especially the carbodiimide method) can be enhanced by adding 1-hydroxybenzotriazole. For example, N-Boc-N-methyl-D-Phe-L-Pro (U.S. Pat. No. 5,391,705, issued Feb. 21, 1995) is dissolved in a suitable organic solvent, such as methylene chloride, under an inert atmosphere, such as nitrogen, optionally in the presence of about one equivalent of 1-hydroxybenzotriazole (HOBt). To this solution is added about one equivalent of N,N'-dicyclohexylcarbodiimide (DCC) dissolved in a suitable organic solvent, such as methylene chloride. The reaction mixture is allowed to stir for about 1 to 15 hours. To the mixture is added 1 to 4 equivalents of a suitable base such as N-methylmorpholine or triethylamine and at least one molar equivalent of, N-9-[1-[3-[bis($K_1$-protected)-amino]methylene]amino]-6-amino-5-hydroxy-4,4-difluorononane 2, dissolved in a suitable organic solvent such as methylene chloride. The reaction mixture is then allowed to stir for about 1 to 15 hours. The coupled product, N-$K_2$-protected-N-methyl-D-phenylalanyl-N-[1-[3-[[bis[($K_1$-protected)amino]methylene]amino]propyl]-3,3-difluoro-2-hydroxyhexyl]-L-prolinamide 3, is then isolated and optionally purified by techniques well known in the art such as extractive techniques, precipitation, crystallization and chromatography.

In Scheme A, step c, N-$K_2$-protected-N-methyl-D-phenylalanyl-N-[1-[3-[[bis[($K_1$-protected)amino]methylene]-amino]propyl]-3,3-difluoro-2-hydroxyhexyl]-L-prolinamide 3 is reacted with an appropriate oxidizing agent to provide N-$K_2$-protected-N-methyl-D-phenylalanyl-N-[1-[3-[[bis[($K_1$-protected)amino]methylene]amino]propyl]-3,3-difluoro-2-oxohexyl]-L-prolinamide 4.

For example, N-$K_2$-protected-N-methyl-D-phenylalanyl-N-[1-[3-[[bis[($K_1$-protected)amino]methylene]amino]propyl]-3,3-difluoro-2-hydroxyhexyl]-L-prolinamide 3 is reacted with an appropriate oxidizing agent, such as periodinane, a chromic anhydride pyridine complex, pyridinium dichromate, or a dimethyl sulfoxide complex, such as DMSO-(COCl)$_2$ (Swern conditions), to provide N-$K_2$-protected-N-methyl-D-phenylalanyl-N-[1-[3-[[bis[($K_1$-protected)amino]methylene]-amino]propyl]-3,3-difluoro-2-oxohexyl]-L-prolinamide 4 using standard oxidizing techniques well known and appreciated by those skilled in the art. Standard oxidizing techniques include procedures such as the Swern oxidation procedure, *Synthesis*, 165 (1981); the Dess Martin periodinane reaction, Dess Martin, *J. Org. Chem.* 48, 4155 (1983); and the Jones oxidation procedure (see U.S. Pat. No. 5,391,705); with the Swern oxidation procedure being most preferred. For example, approximately 1.5 equivalents of oxalyl chloride is dissolved in a suitable anhydrous organic solvent, such as methylene chloride, and cooled to a temperature of from about −55° C. to about −78° C. To this solution is added from about 3 to about 8 equivalents of methyl sulfoxide dropwise, maintaining the temperature at about −55° C. or below. An equivalent of N-$K_2$-protected-N-methyl-D-phenylalanyl-N-[1-[3-[[bis[($K_1$-protected)amino]-methylene]amino]propyl]-3,3-difluoro-2-hydroxyhexyl]-L-prolinamide 3 is dissolved in a suitable amount of anhydrous organic solvent, such as methylene chloride, and added slowly to the reaction with stirring. After addition is complete the reaction is stirred approximately 30 minutes at a temperature of from about −55° C. to about −78° C., an excess of a suitable organic base, such as triethylamine or N-methylmorpholine, is added and the reaction is allowed to warm to room temperature. The oxidized product, N-$K_2$-protected-N-methyl-D-phenylalanyl-N-[1-[3-[[bis[($K_1$-protected)amino]methylene]amino]propyl]-3,3-difluoro-2-oxohexyl]-L-prolinamide 4 is then isolated and purified by techniques well known to one skilled in the art such as extractive techniques, precipitation, crystallization and chromatography.

In Scheme A, step d, N-$K_2$-protected-N-methyl-D-phenylalanyl-N-[1-[3-[[bis[($K_1$-protected)amino]methylene]-amino]propyl]-3,3-difluoro-2-oxohexyl]-L-prolinamide 4 is reacted with a suitable deprotecting agent to provide N-methyl-D-phenylalanyl-N-[1-[3-[(aminoiminomethyl)amino]-propyl]-3,3-difluoro-2-oxohexyl]-L-prolinamide 5.

For example, N-$K_2$-protected-N-methyl-D-phenylalanyl-N-[1-[3-[[bis[($K_1$-protected)amino]methylene]amino]propyl]-3,3-difluoro-2-oxohexyl]-L-prolinamide 4 is reacted with a suitable deprotecting agent, such as hydrochloric acid in either dioxane or ethyl acetate or trifluoroacetic acid either neat or in dichloromethane. Conditions for cleavage of protecting groups for amino protecting groups are described in Greene, "Protective Groups in Organic Chemistry", Chapter 7, John Wiley & Sons, New York (1981). For example, N-$K_2$-protected-N-methyl-D-phenylalanyl-N-[1-[3-[[bis[($K_1$-protected)amino]methylene]amino]propyl]-3,3-difluoro-2-oxohexyl]-L-prolinamide 4 is dissolved in hydrochloric acid/ethylacetate, stirred for about one to several hours. Anhydrous hydrochloric acid is then bubbled into the reaction mixture for about 10–15 minutes, the reaction mixture is stirred for about 20–40 minutes and then concentrated. The residue is then dissolved in water and optionally neutralized with sodium bicarbonate. The deprotected product, N-methyl-D-phenylalanyl-N-[1-[3-[(aminoiminomethyl)amino]propyl]-3,3-difluoro-2-oxohexyl]-L-prolinamide 5 is then isolated and purified by techniques well known to one skilled in the art such as extractive techniques, precipitation, crystallization and chromatography. One of ordinary skill in the art can form pharmaceutically acceptable salts of N-methyl-D-phenylalanyl-N-[1-[3-[(aminoiminomethyl)amino]propyl]-3,3-difluoro-2-oxohexyl]-L-prolinamide 5 using techniques and procedures well known in the art.

The 9,6-diamino-5-hydroxy-4,4-difluorononane, bis-hydrochloride 1 intermediate required for preparation of the end product 5 can be obtained by using a modified Dakin-West reaction as illustrated in U.S. Pat. No. 5,391,705 and set forth in Scheme B. The reagents, starting materials and techniques used in this process are readily available to one of ordinary skill in the art.

SCHEME B

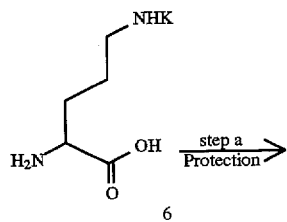

6

9
-continued
SCHEME B

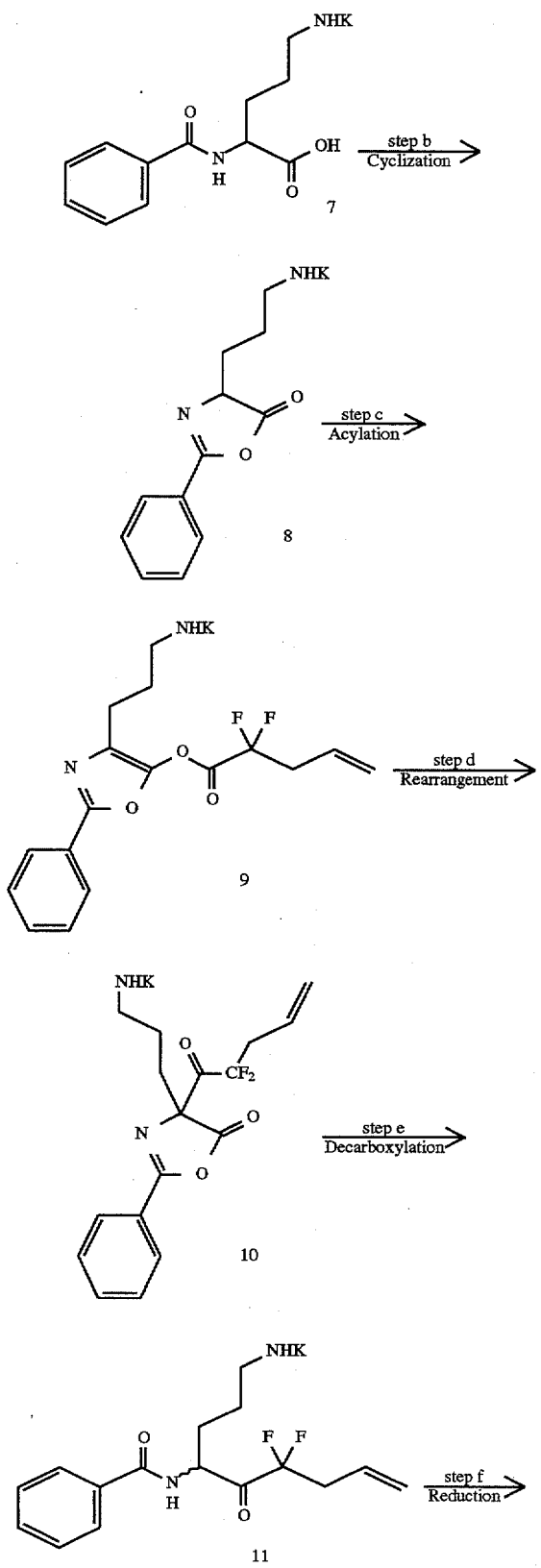

10
-continued
SCHEME B

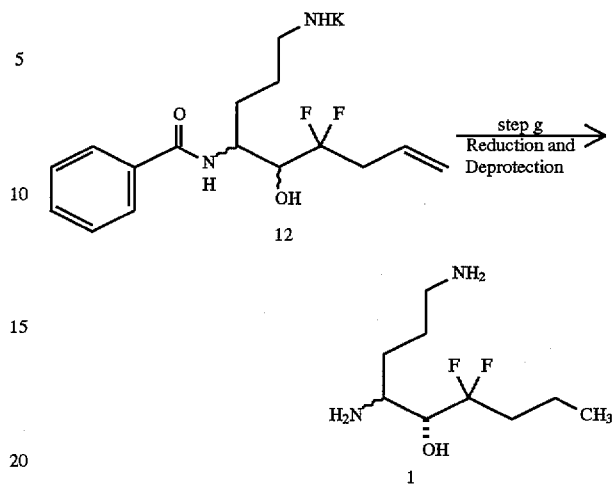

In Scheme B, step a, δ-K-L-ornithine 6 is $N^\alpha$-protected according to standard N-protecting techniques well-known and appreciated by one skilled in the art to provide $N^\alpha$-K-$N^\delta$-benzlocarbonyl-ornithine 7 wherein K refers to a suitable protecting group as described previously in Scheme A, step a, preferably Cbz.

For example, δ-Cbz-L-ornithine 6 is $N^\alpha$-protected using benzoyl chloride and standard Schotten-Baumann conditions. Specifically, a solution of benzoyl chloride in an ethereal solvent, such as diethyl ether, is added concomitantly with sodium hydroxide to a solution of δ-Cbz-L-ornithine 6 in sodium hydroxide, over a period of from about 0.5 to 1 hours, while maintaining the reaction temperature between 0° C. to about 5° C. The reaction mixture is then stirred for approximately 4 hours at room temperature, extracted with an ethereal solvent such as diethyl ether and acidified to about pH 1 using concentrated hydrochloric acid solution. Additional water is then added and the mixture is allowed to stand for approximately 48 hours. The solids are collected and purified by techniques well known to one skilled in the art to provide $N^\alpha$-K-$N^\delta$-benzyloxycarbonyl-ornithine 7.

In Scheme B, step b, $N^\alpha$-K-$N^\delta$-benzyloxycarbonyl-ornithine 7 is cyclized to provide 2-phenyl-[4-(3-K-aminopropyl)]-5-(4H)-oxazolane 8.

For example, a slurry of $N^\alpha$-K-$N^\delta$-benzyloxycarbonyl-ornithine 7 in a suitable organic solvent, such as methylene chloride, is contacted with about 0.1 to 1.0 molar equivalents of dicyclohexylcarbodiimide. The reaction mixture is then stirred for about 2 to 5 hours and the resulting precipitated dicyclohexylurea by-product is filtered and washed with a suitable organic solvent, such as methylene chloride. The filtrate is then concentrated and diluted with a suitable ethereal solvent, such as diethyl ether and the process is optionally repeated. The cyclized product, 2-phenyl-[4-(3-K-aminopropyl)]-5-(4H)-oxazolane 8, is then isolated and purified by techniques well known to one skilled in the art such as precipitation and crystallization.

In Scheme B, step c, 2-phenyl-[4-(3-K-aminopropyl)]-5-(4H)-oxazolane 8 is acylated according to standard acylation techniques to provide the corresponding O-acyl compound of structure 9.

For example, a suitable tertiary amine, such as triethylamine, is added to a solution of 2-phenyl-[4-(3-K-aminopropyl)]-5-(4H)-oxazolane 8 in a suitable organic solvent, such as tetrahydrofuran or tetrahydrofuran/heptane mixtures, at a temperature range of from about −10° C. to about 10° C. under an inert atmosphere, preferably nitrogen. A solution of α,α-difluoropentenoyl chloride, or the corresponding anhydride, in a suitable organic solvent, such as heptane, is slowly added to the reaction mixture while maintaining the reaction temperature between about −10° C. and 10° C. After about 30 to 60 minutes, the reaction mixture is allowed to warm to room temperature and stirred for about another 30 minutes. The triethylamine hydrochloride salt is removed by extractive techniques well known in the art, such as filtration, and the filtrate is concentrated to give the corresponding O-acyl compound of structure 9.

In Scheme B, step d, the corresponding O-acyl compound of structure 9 is optionally reacted with an acylation catalyst to provide the corresponding C-acyl compound of structure 10.

For example, the corresponding O-acyl compound of structure 9 is dissolved in a suitable organic solvent, such as tetrahydrofuran and contacted with an acylation catalyst, such as a dialkylaminopyridine, preferably 4-dimethylaminopyridine (DMAP). The reaction mixture is then stirred for about 2–4 hours at room temperature to produce the C-acyl compound of structure 10, which is used without further isolation or purification.

In Scheme B, step e, the C-acyl compound of structure 10, is decarboxylated with a decarboxylating agent such as oxalic acid, succinic acid, and the like, with oxalic acid being preferred, to provide $N^\delta$-9-K-amino-6-benzamido-5-oxo-4,4-difluoro-1-nonene 11.

For example, a solution containing from 1 to 5 molar equivalents of dried oxalic acid in a suitable organic solvent, such as tetrahydrofuran is added to the reaction mixture from Scheme B, step d, containing the C-acyl compound of structure 10, and is left stirring for 16–32 hours. The reaction mixture is then concentrated and treated with a suitable acid, such as hydrochloric acid, and extracted with ethyl acetate. The layers are separated and the organic layer is washed with an appropriate base such as sodium carbonate, sodium bicarbonate or sodium hydroxide, optionally washed with brine, dried with a suitable drying agent such as magnesium sulfate and concentrated. The decarboxylated product, $N^\delta$-9-K-amino-6-benzamido-5-oxo-4,4-difluoro-1-nonene 11, is then isolated and purified by techniques well known to one skilled in the art such as precipitation and crystallization.

In Scheme B, step f, $N^\delta$-9-K-amino-6-benzamido-5-oxo-4,4-difluoro-1-nonene 11, is contacted with an appropriate reducing agent to provide $N^\delta$-9-K-amino-6-benzamido-5-hydroxy-4,4-difluoro-1-nonene 12.

As is well known and appreciated in the art, this reduction will give a 5-hydroxy derivative that is a mixture of stereoisomers at the 5-position.

Appropriate reducing agents are well known in the art and include but are not limited to lithium tri-t-butyloxyaluminohydride, potassium borohydride, lithium tri-sec-butylborohydride, lithium borohydride, sodium borohydride, and lithium triethylborohydride with sodium borohydride being preferred.

For example, $N^\delta$-9-K-amino-6-benzamido-5-oxo-4,4-difluoro-1-nonene 11 is contacted with a molar excess of an appropriate reducing agent. The reaction is carried out in a suitable solvent. Suitable solvents for hydride reductions are well known in the art, such as toluene, diethyl ether, methyl t-butyl ether, tetrahydrofuran (THF) and tetrahydrofuran/ethanol mixtures. The reaction is carried out at a temperature in the range of from −78° C. to about 10° C. The reduced product, $N^\delta$-9-K-amino-6-benzamido-5-hydroxy-4,4-difluoro-1-nonene 12 may be isolated from the reaction zone by extraction and then purified by methods well known in the art, such as chromatography and recrystallization.

In Scheme B, step g, $N^\delta$-9-K-amino-6-benzamido-5-hydroxy-4,4-difluoro-1-nonene 12 is contacted with an appropriate alkylene reducing agent and an appropriate deprotecting agent to provide 9,6-diamino-5-hydroxy-4,4-difluorononane 1.

An appropriate alkylene reducing agent includes diborane, diisoalkyl borane, borane/tertiary amine complexes and hydrogen in the presence of a hydrogenation catalyst. The most preferred alkylene reducing agent is hydrogen in the presence of a hydrogenation catalyst. Examples of hydrogenation catalysts include platinum, palladium, rhodium, ruthenium and nickel. Both the metals, as finely dispersed solids or adsorbed on inert supports such as carbon or alumina, and certain soluble complexes of these metals exhibit catalytic activity.

An appropriate deprotecting agent includes those described previously in Scheme A, step d. Other deprotecting agents, as well as conditions for cleavage of protecting groups are well known in the art and are described in Greene, "Protective Groups in Organic Chemistry", Chapter 7, John Wiley & Sons, New York (1981).

For example, $N^\delta$-9-K-amino-6-benzamido-5-hydroxy-4,4-difluoro-1-nonene 12 is dissolved in a suitable alcohol, such as isopropanol and a suitable acid such as hydrochloric acid. The solution is then treated with an alkylene reducing agent, such as palladium dihydroxide adsorbed on an inert carbon support, and shaken under hydrogen gas (40–60 psi) for about 20 to 30 hours. The reaction mixture is filtered and concentrated to yield a $N^\alpha$-benzoyl-difluoro alcohol, hydrochloride. The $N^\alpha$-benzoyl-difluoro alcohol, hydrochloride is then contacted with an appropriate deprotecting agent, such as hydrochloric acid and heated to reflux. The reaction mixture is cooled to room temperature, filtered and the filtrate is extracted with diethyl ether and the layers separated. The aqueous layer is treated with activated carbon, heated, filtered and concentrated to provide 9,6-diamino-5-hydroxy-4,4-difluorononane 1. One of ordinary skill in the art can form pharmaceutically acceptable salts of 9,6-diamino-5-hydroxy-4,4-difluorononane 1 using techniques and procedures well known in the art.

The α,α-difluoropentenoyl chloride intermediate 8a, required for preparation of the O-acyl compound of structure 9 can be obtained as illustrated in U.S. Pat. No. 5,391,705 and set forth in Scheme C. The reagents, starting materials and techniques used in this process are readily available to one of ordinary skill in the art.

SCHEME C

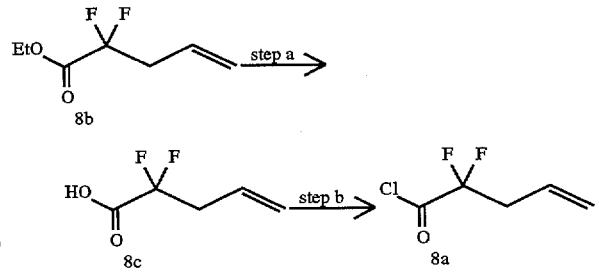

In Scheme C, step a, 2,2-difluoro-4-pentenoic acid 8c, is prepared by hydrolysis of ethyl α,α-difluoropentenoate 8b (U.S. Pat. No. 5,391,705, issued Feb. 21, 1995) by techniques and procedures well known in the art, such as base hydrolysis.

For example, from about 1.0 to 1.5 molar equivalents of a suitable base, such as a lithium hydroxide, is added to a solution of ethyl α,α-difluoropentenoate 8b, also known as ethyl 2,2-difluoro-4-pentenoate (U.S. Pat No. 4,847,401, siiued Jul. 11, 1989), in water at a temperature of from about −10° C. to about 10° C. The reaction mixture is allowed to warm to room temperature for about 2 to 4 hours and then heated at about 40° C. to about 55° C. for an additional 2 to 4 hours. Ethanol and water are removed from the reaction mixture and 2,2-difluoro-4-pentenoic acid 8c may be isolated from the reaction zone by extraction and then purified by methods well known in the art.

In Scheme C, step b, 2,2-difluoro-4-pentenoic acid 8c is contacted with a suitable chlorinating agent to yield 2,2-difluoro-4-pentenoyl chloride 8a.

An appropriate chlorinating agent is one that converts a hydroxyl group to a chloro group and does not cause the degradation of the starting material or the product. Appropriate chlorinating agents include phosphorous trichloride, thionyl chloride, oxalyl chloride and the like.

For example, 2,2-difluoro-4-pentenoic acid 8c is contacted with about 1.0 to 1.5 molar equivalents of an appropriate chlorinating agent. The reaction is carried out in a suitable solvent, such as dichloromethane, toluene or dimethylformamide. The reaction is carried out at a temperature of from about 20° C. to about 35° C. and generally requires about 4 to 24 hours. The product, 2,2-difluoro-4-pentenoyl chloride 8a, can be isolated by fractional distillation and purified by techniques well known in the art, such as chromatography.

N-methylated α-amino acids can be prepared as described in Scheme D and generally in B.S. Pitzele et al., *J. Med. Chem.*, 37, 888–896 (1994), herein incorporated by reference as if fully set forth. All of the substituents, unless otherwise indicated, are previously defined. The reagents and starting materials are readily available to one of ordinary skill in the art.

SCHEME D

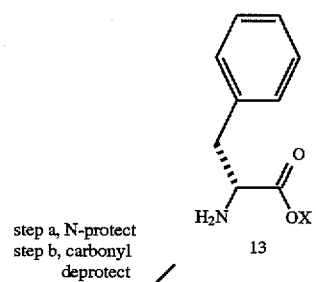

step a, N-protect
step b, carbonyl deprotect

-continued
SCHEME D

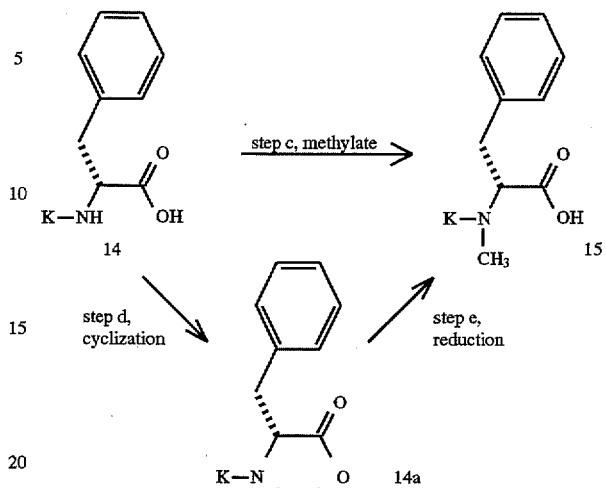

In Scheme D, step a, an α-amino acid of structure 13 wherein X is a suitable α-carboxyl protecting group, such as a methyl ester or a solid phase resin, is coupled with a suitable protecting group "K", previously defined in Scheme A, step a, in a manner analogous to the procedures described in Scheme A, step b to provide the coupled product.

In Scheme D, step b, the coupled product is deprotected or cleaved from the solid phase under conditions well known in the art to provide the acid of structure 14. For example, wherein X is a methyl or ethyl group on structure 13, the compound is dissolved in a suitable organic solvent, such as ethanol and treated with approximately an equal volume of water. To this solution, with stirring is added 1 to 2 equivalents of lithium hydroxide and the reaction is allowed to stir for 1 to 6 hours. The resulting acid is then isolated and purified by techniques well known in the art. For example, the organic solvent is removed under vacuum and the remaining aqueous solution is acidified with dilute hydrochloric acid. The aqueous phase is then extracted with a suitable organic solvent, such ethyl acetate, and the combined organic extracts are dried over anhydrous magnesium sulfate, filtered and concentrated under vacuum. The residue can then be purified by flash chromatography on silica gel with a suitable eluent, such as methanol/chloroform to provide the acid of structure 14.

In Scheme D, step c, the acid 14 is N-methylated to provide the N-protected N-methylated compound of structure 15. For example, the acid 14 is dissolved in a suitable organic solvent, such as tetrahydrofuran, cooled to about 0° C. and treated with excess methyl iodide. Then 1 to 3 equivalents of sodium hydride is added to the solution which is stirred for about 10 minutes at 0° C. and then warmed to room temperature and stirred for 24 to 48 hours. The product is then isolated by techniques well known in the art, such as extractive methods. For example, dilute aqueous hydrochloric acid is added and the reaction is extracted with a suitable organic solvent, such as ethyl acetate. The organic extracts are then combined, washed with 5% sodium thiosulfate, brine, dried over anhydrous magnesium sulfate, filtered through a pad of silica gel and concentrated under vacuum to provide the N-protected, N-methylated compound 15.

Alternatively, the N-protected N-methylated compound 15 can be prepared following the procedure described in Scheme D, steps d and e, from the acid of structure 14.

In Scheme D, step d, the acid 14 is cyclized to provide the oxazolidine described by structure 14a. For example, the acid 14 is dissolved in a suitable organic solvent, such as benzene and treated with an excess of paraformaldehyde. To this is added about 0.2 to 0.4 equivalents of p-toluenesulfonic acid and the reaction is heated at reflux for about 23 hours with continuous removal of water using a Dean-Stark trap. The reaction is then allowed to cool to room temperature and the product is isolated and purified by techniques well known in the art. For example, the cooled reaction is concentrated under vacuum, the residue taken up in a suitable organic solvent, such as ethyl acetate, rinsed with saturated sodium bicarbonate, the organic phase dried over anhydrous magnesium sulfate, filtered and concentrated under vacuum. The residue is then purified by flash chromatography on silica gel with a suitable eluent, such as ethyl acetate/hexane to provide the oxazolidine 14a.

In Scheme D, step e, the oxazolidine 14a is reduced under conditions well known in the art to provide the N-protected N-methylated compound 15. For example, the oxazolidine 14a is dissolved in a suitable organic solvent, such as chloroform and treated with excess trifluoroacetic acid. To the solution is added an excess of triethylsilane with stirring at room temperature. The reaction is allowed to stir for 1 to 7 days and then concentrated under vacuum to provide the N-protected N-methylated compound 15.

The following examples present typical syntheses as described in Schemes A–D. These examples are understood to be illustrative only and are not intended to limit the scope of the present invention in any way.

As used herein, the following terms have the indicated meanings: "g" refers to grams; "mmol" refers to millimoles; "mL" refers to milliliters; "bp" refers to boiling point; "mp" refers to melting point; "°C." refers to degrees Celsius; "mm Hg" refers to millimeters of mercury; "µL" refers to microliters; "µg" refers to micrograms; and "µM" refers to micromolar; "eq" refers to molar equivalents; "conc" refers to concentrated; "sat" refers to saturated.

EXAMPLE 1

Preparation of 2,2-Difluoro-4-pentenoic acid 8c

Scheme C, step a: To a solution of ethyl α,α-difluoropentenoate 8b (80 g, 0.49 mol, U.S. Pat. No. 4,847,401, issued Jul. 11, 1989) in $H_2O$ (80 mL) is added LiOH (20.9 g, 0.5 mol) over 5 min at 0°–5° C. The reaction mixture is allowed to warm to room temperature for 3 h, then heated at 45°–50° C. for 3 h. Ethanol and $H_2O$ are removed (60 torr, 45° C.) from the reaction mixture. The resulting orange oil is dried (1 torr, room temperature) for 2 h to obtain an oily solid. The oily solid is diluted in $H_2O$ (75 mL) and acidified to pH 1 using conc HCl. The reaction mixture is extracted with diethyl ether (3×150 mL). Conc HCl is added to the aqueous layer until it is pH 1 and the aqueous layer is extracted again with diethyl ether (3×100 mL). The combined organic layers are dried ($MgSO_4$), concentrated to an oil and distilled (140°–170° C.) to obtain 58.8 g, 432 mmol of the title compound 8c as an oil in 88% yield. $^{19}F$ NMR ($CDCl_3$) δ −106.8 (t)($CFCl_3$ as ref); $^{13}C$ NMR ($CDCl_3$) δ 168.3 (t, $CO_2H$), 126.4 (s, C=C), 122.3 (s, C=C), 115.0 (t, $CF_2$), 38.9 (t, $CH_2$); $^1H$ NMR ($CDCl_3$) δ 2.88 (m, $CH_2$, 2H), 5.28 (m, 1H), 5.32 (s, 1H), 5.76 (m, 1H), 8.74 (s, 1H).

EXAMPLE 2

Preparation of 2,2-Difluoro-4-pentenoyl chloride 8a

Scheme C, step b: Add oxalyl chloride (17.6 mL, 201.8 mmol) to compound 8c (25 g, 183.7 mmol) and dimethylformamide (3 drops) under neat conditions at room temperature. Observe gas evolution for approximately 2 h. After 5 h, treat the reaction mixture with an additional 0.08 eq of oxalyl chloride (1.2 mL) and stir for 18 h. Use fractional distillation (88°–91° C.) to obtain 24.4 g, 158 mmol of the title compound 8a as an oil in 85% yield. 19F NMR (CDCl3) δ −101.9 (t); $^{13}C$ NMR ($CDCl_3$) δ 167.3 (t, $CO_2H$), 125.5 (s, C=C), 123.1 (s, C=C), 115.6 (t, $CF_2$), 38.3 (t, $CH_2$); $^1H$ NMR ($CDCl_3$) δ 2.90 (m, 2H), 5.33 (d, 1H), 5.36 (s, 1H), 5.74 (m, 2H).

EXAMPLE 3

Preparation of $N^\alpha$-Benzoyl-N-$^\delta$-benzyloxycarbonyl-ornithine 7 (K=Cbz.)

Scheme B, step a: To a solution of δ-Cbz-L-ornithine 6 (50 g, 187.8 mmol, Advanced ChemTech, Louisville, Ky. 40228-1075) in 1N sodium hydroxide (250 mL, 0.25 mol) is added a solution of benzoyl chloride (22 mL, 189.5 mmol) in diethyl ether (200 mL) and 1N NaOH (313 mL, 0.31 mol) simultaneously over a period of 45 min maintaining the reaction temperature between 0°–5° C. Stir the reaction mixture at room temperature for 4 h, extract with diethyl ether (3×100 mL) and separate the organic phase. Wash the aqueous phase with diethyl ether (3×100 mL) and acidify to pH 1 using conc HCl solution to form white solids. Add additional water (450 mL) and allow the mixture to stand for 48 h. Collect the white solids, wash with water (200 mL) and diethyl ether (200 mL) and dry at 109° C. (10 torr) overnight to provide 64.04 g, 173.9 mmol of title compound 7 as a white solid in 92% yield. MS-FAB m/z (% relative intensity) 371 ($M^+$+1, 25%), 393 ($M^+$+Na, 100%); $^1H$ NMR ($CDCl_3$) δ 7.9 (m, 2H, aroyl), 7.7 (d, J=8 Hz, 1H, NH), 7.5–7.2 (m, 8H, aroyl, aryl), 6.3 (m, 1H, NH), 5.1 (s, 2H, benzyl), 4.7 (m, 1H, CH), 3.20 (q, 2H, $NCH_2$), 2.1–1.8, 1.8–1.6 (2m, 4H, $CH_2$—$CH_2$).

EXAMPLE 4

Preparation of 2-Phenyl-[4-(3-benzyloxycarbonylaminopropyl)]-5-(4H)-oxazolane 8 (K=Cbz)

Scheme B, step b: To a slurry of $N^\alpha$-benzamide 7 (25 g, 676.5 mmol) in methylene chloride (250 mL) is added N,N'-dicyclohexylcarbodiimide (14.63 g, 70.9 mmol) in four portions. Observe an exotherm (5°–10° C.) while stirring the reaction mixture for 3 h. The precipitated dicyclohexylurea is filtered and washed with methylene chloride (100 mL). Concentrate the filtrate to a yellow oil, dilute with diethyl ether (200 mL), filter and concentrate the filtrate to give a light yellow oil. Dilute the oil with diethyl ether (150 mL) and filter the remaining dicyloherylurea. Allow the filtrate to crystallize overnight under Argon. Collect and dry (1 torr) the crystallized product to provide 20.86 g, 59.2 mmol of the title compound 8 as a white solid in 88% yield. MS (CI,$CH_4$) m/z (% relative intensity) 353 ($M^+$+1, 100%). Anal. Calcd for $C_{20}H_{20}N_2O_4$ (352.30): C, 68.17; H, 5.72; N, 7.95. Found C, 68.02; H, 5.77; N, 7.93; 1H NMR (CDCl3) δ 8.0 (d, J=8 Hz, 2H, aroyl), 7.65–7.2 (m, 8H, aroyl, aryl), 5.1 (s (with shoulder), 3H, benzyl, NH), 4.4 (m, 1H, CH), 3.3 (m, 2H, $NCH_2$), 2.2–2.0 (m, 1H), 1.95–1.6 (m, 3H, $CH_2$—$CH_2$).

EXAMPLE 5

Preparation of $N^\delta$-9-Benzyloxycarbonylamino-6-benzamido-5-oxo-4,4-difluoro-1-nonene 11 (K=Cbz)

Scheme B, steps c, d and e: To a solution of azalactone 8 (33.6 g, 95.2 mmol) in tetrahydrofuran (80 mL) and heptane (70 mL), add triethylamine (16 mL, 115 mmol) at 0° C. under nitrogen. Slowly add a solution of 2,2-Difluoro-4-pentenoyl chloride 8a (19.2 g, 124.2 mmol) in heptane (40 mL) to the reaction mixture while maintaining the reaction temperature between 0°–3° C. After 45 min, allow the reaction mixture to warm to room temperature and stir for another 30 min. Remove a small aliquot, dry for 10 min (5 torr, room temperature) and analyze by HPLC, $^1H$ NMR, $^{19}F$ NMR to detect O-acylation of the azlactone. Remove the triethylamine.HCl by filtration and concentrate the filtrate to give a light orange-yellow oil. Analyze a sample of the oil by HPLC, $^1$H NMR, $^{19}$F NMR to confirm formation of the O-acyl intermediate 9. Dissolve the oil in tetrahydrofuran (60 mL), treat with 4-dimethylaminopyridine (1.74 g, 14.2 mmol) and stir for 3 h at room temperature. Remove a small aliquot, dry for 15 min (5 torr, room temperature) and analyze by HPLC, $^1$H NMR, $^{19}$F NMR to confirm the transfer of the O-acyl intermediate 9 to the C-acyl intermediate 10. Add a solution of dried oxalic acid (25.76 g, 286.1 mmol) in tetrahydrofuran (60 mL) to the reaction mixture and stir for 24 h. Remove a small aliquot, filter and dry (1 torr, room temperature) and analyze by $^1$H NMR and $^{19}$F NMR. Concentrate the reaction mixture to ¼ volume treat with 10% aq HCl (200 mL), extract with ethyl acetate (150 mL) and separate the layers. Wash the organic layer with sat aq NaHCO$_3$ (250 mL), brine (250 mL), dry (MgSO$_4$) and concentrate to provide an orange oil. Dilute the resulting oil with 4:1 hexane/ethyl acetate and allow to stand overnight to provide white solids. Collect and dry (1 torr, room temperature) the product to provide 21.7 g, 48.8 mmol of the title compound 11 as a light yellow solid in 51% yield. Concentrate the filtrate to give an oil. The crude oil is pre-absorbed on silica gel (2 g SiO$_2$/1 g oil) and purified by flash chromatography using a 10 cm O.D. column containing 6 inches of silica in height and eluting with 3:2 hexane/ethyl acetate to provide 15.4 g, 34.65 mmol of title compound 11 as a light yellow solid in 36% yield. Total yield of title compound 11 is 37.1 g (87%). MS (CI, CH$_4$) m/z (% relative intensity) 445 (M$^+$+1, 100%). Anal. Calcd for C$_{24}$H$_{26}$N$_2$O$_4$F$_2$ (444.49): C, 64.85; H, 5.90; N, 6.30. Found C, 64.74; H, 5.86; N, 6.20; $^{19}$F NMR (CDCl$_3$) δ −109.3 (dt, J=17, 270 Hz), −103.6 (dt, J=17, 270 Hz), $^1$H NMR (CDCl$_3$) δ 7.8 (m, 2H, aroyl), 7.6–7.4 (m, 3H, aroyl), 7.3 (s, 5H, aryl), 7.1 (m, 1H, NH), 5.9–5.1 (m, 1H, CH=C), 5.35–5.15 (m, 2H, C=CH$_2$), 5.1 (s, 2H, benzyl), 4.95 (m, 1H, CH), 3.3 (m, 2H, NCH$_2$), 2.9 (m, 2H, CF$_2$CH$_2$), 2.1, 1.7 (2m, 4H, CH$_2$—CH$_2$).

EXAMPLE 6
Preparation of N-9-Benzyloxycarbonylamino-6-benzamido-5-hydroxy-4,4-difluro-1-nonene 12 (K=Cbz)

Scheme B, step f: To a solution of difluoroketone 11 (38.0 g, 85.5 mmol) in ethanol (500 mL) and tetrahydrofuran (20 mL) is added NaBH$_4$ (1.66 g, 43.88 mmol) at 0° C. A precipitate forms with 1 h upon warming to room temperature. Dilute the heterogeneous reaction mixture using tetrahyrofuran (55 mL) to give a mostly homogeneous solution and stir for 0.5 h. Concentrate the reaction mixture to a solid, treat with 10% HCl solution (800 mL) and extract with ethyl acetate (400 mL). Separate the organic phase, dry (MgSO$_4$), filter and concentrate to provide 38.4 g, 86 mmol of title compound 12 (4/1 diastereomeric mixture) as a gray-white solid in quantitative yield. MS (CI, CH$_4$) m/z (% relative intensity) 447 (M$^+$+1, 50%). Anal. Calcd for C$_{24}$H$_{28}$N$_2$O$_4$F$_2$ (446.51): C, 64.56; H, 6.32; N, 6.27. Found C, 64.75; H, 6.25; N, 6.17. $^{19}$F NMR (CDCl$_3$) δ (major diastereomer) −106.9 (ddt), −110.5 (ddt), (minor diastereomer −109.1 (m); $^1$H NHR (CDCl$_3$) δ 7.8 (m, 2H, aroyl), 7.6–7.4 (m 8H, aroyl, aryl), 6.9 (m, 1H, NH), 5.9–5.7 (m, 1H, CH=C), 5.3 (m, 2H, CH$_2$=C), 5.1 (s, 2H, benzyl), 4.4 (m, 1H, CHN), 4.0, 3.9 (2m, 1H, CHCF$_2$), 3.2 (m, 2H, NCH$_2$), 2.9–2.6 (m, 2H, CHF$_2$CH$_2$), 1.8 (m, 2H), 1.6 (m, 2H, CH$_2$).

EXAMPLE 7
Preparation of 9-Amino-6-benzamido-5-hydroxy-4,4-difluronoanne, hydrochloride Scheme B, step g (reduction and deprotection): Dissolve a solution of difluoro alcohol 12 (38 g, 85.1 mmol) in isopropanol (800 mL) and 1N HCl (200 mL). Treat the solution with 10% Pd(OH)$_2$/C (3.81 g) and shake under hydrogen (45 psi) for 28 h. Filter the reaction mixture through celite and concentrate (1 torr, room temperature) to provide 29.9 g, 85.4 mmol, of title compound as an off-white solid in quantitative yield. MS (CI, CH$_4$) m/z (% relative intensity) 315 (M$^+$+1, 100%). Anal. Calcd for C$_{16}$H$_{24}$N$_2$O$_2$F$_2$ (350.84): C, 54.78; H, 7.18; N, 7.98. Found C, 54.47; H, 7.28; N, 7.83; $^{19}$F NMR (CD$_3$OD) δ (major diastereomer) −105.7 (ddt) and −107.9 (m), (minor diastereomer) −107.7 (m) and −110.0 (m); $^1$H NMR (CD$_3$OD) δ 7.9 (m, 2H, aroyl), 7.5 (m, 3H, aroyl), 4.4 (m, 1H, CHN), 3.9 (dr, J=17 Hz, 5 Hz, 1H, CHCF$_2$), 3.0 (m, 2H, NCH$_2$), 2.2–1.4 (2m, 8H, 4CH$_2$), 0.95 (t, J=7 Hz, 3H).

EXAMPLE 8
Preparation of 9,6-Diamino-5-hydroxy-4,4-difluorononane, bis-hydrochloride 1

Scheme B, step g (deprotection): Heat to reflux (110° C.) a solution of 9-Amino-6-benzamido-5-hydroxy-4,4-diflurononane, hydrochloride (26.85 g, 76.5 mmol) in conc aq HCl (250 mL) for 19 h. Benzoic acid crystals develop as the reaction mixture is cooled to room temperature. Remove the crystals by filtration. Extract the filtrate with diethyl ether (250 mL) and separate the layers. Treat the aqueous layer with activated carbon, heat (80° C.), filter through celite, concentrate and dry to provide 21.5 g, 75.9 mmol of title compound 1 as a tan solid in quantitative yield. MS (CI, CH$_4$) m/z (% relative intensity) 211 (M$^+$+1, 43%); $^{19}$F NMR (CD$_3$OD) δ (major diastereomer) −106.4 (dt) and −110.6 (m), (minor diastereomer) −107.6 (m) and −112.6 (m), $^1$H NMR (D$_2$O) δ 4.0, 3.9 (2t, J=4 Hz, 1H, CHCF$_2$), 3.5 (m, 1H, CHN), 2.9 (m, 2H, NCH$_2$), 2.0–1.5 (m, 6H, 3 CH$_2$), 1.3 (m, 2H, CH$_2$), 0.8 (t, J=7 Hz, 3H).

EXAMPLE 9
Preparation of N-9-[1-[3-[bis[(1,1-dimethylethoxy)carbonyl]amino]methylene]amino]-6-amino-5-hydroxy-4,4-difluorononane 2 (K$_1$=Boc)

Scheme A, step a: Add triethylamine (33 mL, 2 eq) to a solution of diamine bis-hydrochloride 1 (34.4 g, 0.122 mol) in dimethylformamide (250 mL), added at 0° C. After 5 min, treat the reaction mixture with a solution of bis-Boc amidinopyrazole (36.93 g, 0.119 mol) in dimethylformamide (90 mL) along with simultaneous addition of triethylamine (17 mL, 1 eq), added at 0° C. Allow the reaction mixture to warm to room temperature and stir overnight. Add aq citric acid (200 mL) to the reaction mixture and extract the mixture with methylene chloride (2×400 mL). Wash the combined organic layers with brine (500 mL) and water (200 mL), dry (Na$_2$SO$_4$), filter and concentrate to provide an oil. Purify by flash chromatography (silica gel; 7:1 CHCl$_3$:MeOH) to give 45.5 g of title compound 2 as a white foam in 83% yield. 19F NMR (CDCl3) δ (major diastereomer) −105.7 (m) and −111.2 (m); 1H NMR (CDCl3) δ 11.4 (m, 1H, NHBoc), 8.3 (m, 1H, NH), 3.6 (t, J=5 Hz, 0.5H, CHCF$_2$), 3.4 (m, 2.5H, CHCF$_2$, NCH$_2$), 2.9 (m, 1H, NCH), 2.0–1.0 (m, 26H, 2Boc, 4CH$_2$), 0.9, 0.8 (2t, J=7 Hz, 3H (4:1 ratio)).

EXAMPLE 10
Preparation of N-[(1,1-dimethylethoxy)carbonyl]-N-methyl-D-phenylalanyl-N-[1-[3-[[bis[[(1,1-dimethylethoxy)carbonyl]-amino]methylene]amino]propyl]-3,3-difluoro-2-hydroxyhexyl]-L-prolinamide 3 (K$_1$=Boc, K$_2$=Boc)

Scheme A, step b: Add N,N'-dicyclohexylcarbodiimide (20.76 g, 100.6 mmol) to a solution of N-Boc-N-methyl-D-Phe-Pro-OH (37.89, 100.6 mmol) and hydroxybenzotriazole (13.59 g, 100.6 mmol) in methylene chloride (800 mL), added at 0° C. Stir the reaction mixture for 4 h. To the reaction mixture, add amino alcohol 2 (45.5 g, 100.6 mmol) in methylene chloride (200 mL) and N-methylmorpholine (11.1 mL, 100.6 mmol) and stir overnight. The precipitated dicylohexylurea is removed by filtration and the filtrate is concentrated to a yellow oil. Dissolve the oil in ethyl acetate (2×250 mL), wash with 10% aq citric acid (2×250 mL), brine (250 mL) and $H_2O$ (150 mL). Separate the organic layer, dry ($Na_2SO_4$), filter and concentrate to provide 88 g of crude title product 3 as a light yellow foam in excess of quantitative yield. Crude title product 3 may be carried to the next step without further purification. $^{19}F$ NMR ($CDCl_3$) δ (major diastereomer) −107.9 (m) and −111.0 (m); $^1H$ NMR ($CD_3OD$) δ 7.3 (m, 5H, $C_6H_5$), 5.1 (m, 1H, CH-phe), 4.5–4.0 (m, 2H, CH-pro, CH-OH), 3.9–3.3, 3.2 (2m, 10H, benzyl, $CH_2$-pro, $CH_2$-N-gua, $CH_2N$, CH-N), 2.2–1.5 (m, 12H, 6$CH_2$), 1.5–1.2 (3br s, 27H, 3 Boc), 0.9 (dt, 3H, J=2, 7 Hz, $CH_3$).

EXAMPLE 11

Preparation of N-[(1,1-dimethylethoxy)-carbonyl]-N-methyl-D-phenylalanyl-N-[1-[3-[[bis[[(1,1-dimethylethoxy)carbonyl]amino]methylene]-amino]propyl]-3,3-difluoro-2-oxohexyl]-L-prolinamide 4 ($K_1$=Box, $K_1$=Boc)

Scheme A, step c: Add a solution of dimethylsulfoxide (42.5 mL, 0.598 mol) in methylene chloride (700 mL) to a solution of oxalyl chloride (26.1 mL, 0.299 mol) in methylene chloride (350 mL), added at −55° C. Stir the reaction mixture for 45 min and then treat with a solution of alcohol 3 (80.84 g, 0.100 mol) in methylene chloride (350 mL) over 30 min. Stir the reaction mixture for an additional 15 min, maintaining the temperature between −50° C. and −60° C., then treat with diphenylethylamine (157 mL, 0.898 mol) at −55° C. over 30 min. After stirring for another 1 h at −55° C., the reaction mixture is homogeneous red-colored. Slowly quench the reaction mixture using 10% aq citric acid solution (250 mL) at 0° C. Extract the organic layer, wash with brine (200 mL), dry ($MgSO_4$) filter and concentrate to provide approximately 80 g of oily foam. Dissolve the foam in a minimum amount of eluent and purify (2×40 g) by flash chromatography (5"×5" $SiO_2$ column; 3:3:2 Hept/$CH_2Cl_2$/EtOAc) to provide 42.9 g of title compound 4 in 53% yield. $^{19}F$ NMR ($CDCl_3$) δ (major diastereomer) −104.5 (m) and −109.7 (m); $^1H$ NMR ($CDCl_3$) δ 11.50 (d, J=5 Hz, 1H, NH-Boc), 9.40 (d, J=6 Hz, 1H, NH), 7.6, 7.2 (2d, J=5 Hz, NH-CHCO (2 isomers)), 5.0, 4.5 (2m, 3H, CH(3)), 3.6–2.7 (m, 9H, 2 $CH_2N$, benzyl, $CH_3N$), 2.3–1.7 (m, 8H, 4 $CH_2$), 1.7–1.1 (m, 31H, 3Boc, 2 $CH_2$), 0.95 (t, J=7 Hz, $CH_3$).

EXAMPLE 12

Preparation of N-methyl-D-phenylalanyl-N-[1-[3-[(aminoiminomethyl)amino]propyl]-3,3-difluoro-2-oxohexyl]-L-prolinamide dihydrochloride monohydrate 5 (MDL 75,579DA)

Scheme A, step d: Dissolve ketone 4 (21.6 g, 0.267 mol) in 2N HCl/EtOAc (470 mL), stopper the flask and stir at room temperature for 60 h. The reaction mixture is light yellow and under pressure when the flask is vented. Bubble anhydrous HCl into the reaction mixture for 10 min, stopper the flask and stir the mixture for 1 h. Concentrate the reaction mixture to a yellow foam, dilute with $H_2O$ (100 mL) and methylene chloride (75 mL) and stir vigorously for 20 min. Remove the methylene chloride layer and repeat the methylene chloride wash (75 mL). Filter the aqueous phase through celite and lyophilize to provide 15.2 g of title compound 5 (MDL 75,579DA) as a white solid in 98% yield by LC/MS using a Delta Pack Column (2.1 mm×150 mm) at 80° C. $^{19}F$ NMR ($D_2O$) δ (major diastereomer) −112.4 (m), (minor diastereomer) −106.2 (m); $^1H$ NMR ($D_2O$) δ 7.4, 7.3 (2m, 5H, $C_6H_5$), 4.9 (m, 0.2H, $CHCOCF_2$), 4.1 (dd, J=13 Hz, 3 Hz, 0.8H, $CHC(OH)_2$—$CF_2$), 4.55 (dd, J=9 Hz, 5 Hz, 1H, CH-phe), 4.35 (m, 1H, CH-pro), 3.5, 2.6 (2m, 2H, $CH_2$-N-pro), 3.25 (m, 2H, $CH_2$-N), 2.70 (s, 3H, $CH_3N$), 2.2–1.4 (m, 12H, 6 $CH_2$), 0.95 (2t, 3H, J=7 Hz, $CH_3$).

EXAMPLE 13

Purity Determinations of MDL 75,579DA Samples By LC/MS Using Electrospray Ionization Liquid chromatography/mass spectrometry (LC/MS) using electrospray ionization (ESI) may be used to analyze batches of MDL 75,579DA prepared using the process of the present invention.

A. HPLC

Dissolve sample of MDL 75,579DA in initial mobile phase at a concentration of approximately 1 mg/mL. To reduce the amount of hydrate formed by contact with water, prepare the sample just prior to analysis. Inject a 50 μL aliquot of this solution using a WISP 715 autosampler (Waters Chromatography), to a Waters Delta Pak narrow bore C18 (2.1 mm×15 cm) column heated to an apparent temperature of 80° C. for analysis.

Prepare mobile phase A as acetonitrile/water (5/95), containing about 0.05% trifluoroacetic acid (TFA), and mobile phase B consisting of acetonitrile/water (95/5), containing about 0.05% TFA. Establish gradient elution at a flow rate of 0.2 mL/min using a Waters 625 HPLC system. Run a linear gradient from 12 to 57% B for over 45 minutes. Monitor the UV absorption at 214 nm on-line using a Waters 486 tunable wavelength detector (0.5 AUFS) equipped with a low dead volume micro-flow cell.

B. Electrospray Mass Spectrometry

Introduce the entire effluent from the HPLC column (0.2 mL/min) into the ESI probe of the Finnigan MAT TSQ 700 triple quadropole mass spectrometer. Roughly situate the ESI syringe needle, holding at 5.5 kV, 2 cm from the stainless steel capillary orifice of the mass spectrometer. This device, which has an internal diameter of 0.5 mm, separates the ESI spray at atmosphere from the high vacuum conditions of the mass spectrometer. To assist the desolvation process hold the capillary at 200° C. during the analysis. Accomplish further desolvation by the use of a nitrogen sheath gas (70 psi) introduced coaxial to the ESI needle. In addition, use an auxiliary gas ($N_2$) flow of 10 mL/min. Acquire mass spectra using Q3 as the scanning quadrupole covering a m/z range of 200 to 1500 in 2 seconds. The voltages to be applied to the conversion dynode and electron multiplier are −15 kV and 1.4 kV, respectively. Accomplish tuning and calibration with a mixture of synthetic peptides using loop injections at a flow rate of 0.2 mL/min.

C. Estimation of Purity

The peak areas of the two main diastereomers of MDL 75,579DA are summed and divided by the total area integrated over the entire analysis, excluding the unretained substances (void peak). This ratio, based as a percentage, serves as the indication of purity. All purity determinations were performed using peak areas observed in the UV absorption profile. Peak integration was performed using the Peak Pro™ integration software provided by CALS data system (Beckman Instruments, Inc.).

A summary of the purity determinations for three samples prepared using the direct guanylation procedure of the present invention is set forth in Table 2.

TABLE 2

Purity of Three Batches of MDL 75,579DA Prepared Using the Process of the Invention

| MDL 75,579DA Batch | % Purity (UV 214 nm) |
| --- | --- |
| C415F-193 | 96.9 |
| C415F-196 | 98.3 |
| C415F-198 | 97.9 |
| | mean 97.7 ± 0.7 |

By using the process of the invention involving a one-step guanylation of 9,6-diamino-5-hydroxy-4,4-difluoro-nonane, bis-hydrochloride, the Dakin-West route known in the art (U.S. Pat. No. 5,391,705) is shortened by two chemical steps and one chromatography. More dramatically, the overall yield starting from the N-9-[1-[3-[bis[(1,1-dimethylethoxy) carbonyl]amino]methylene]amino]-6-amino-5-hydroxy-4, 4-difluorononane intermediate is increased from about 15% using the art-known Dakin-West procedure to about 43% using the process of the present invention, while achieving, a highly purified final product of about 98% purity.

What is claimed is:

1. A process for preparing N-methyl-D-phenylalalyl-N-[1-[3-[(aminoiminomethyl)amino]propyl]-3,3-difluoro-2-oxohexyl]-L-prolinamide or a pharmaceutically acceptable salt thereof comprising the steps of:

(a) reacting 9,6-diamino-5-hydroxy-4,4-difluorononane, or a pharmaceutically acceptable salt thereof, with an appropriate guanylating agent to provide N-9-[1-[3-[bis($K_1$-protected)amino]methylene]amino]-6-amino-5-hydroxy-4,4-difluorononane, wherein $K_1$ is an N-protecting group suitable for protecting the nitrogens of guanyl moieties;

(b) coupling the N-9-[1-[3-[bis($K_1$-protected)amino]-methylene]amino]-6-amino-5-hydroxy-4,4-difluorononane with N-$K_2$-protected-N-methyl-D-phenylalanyl-L-prolinamide to provide N-$K_2$-protected-N-methyl-D-phenylalanyl-N-[1-[3-[[bis[($K_1$-protected)amino]methylene]amino]propyl]-3,3-difluoro-2-hydroxyhexyl]-L-prolinamide, wherein $K_2$ is an N-protecting group;

(c) reacting N-$K_2$-protected-N-methyl-D-phenylalanyl-N-[1-[3-[[bis[($K_1$-protected)amino]methylene]amino] propyl]-3,3-difluoro-2-hydroxyhexyl]-L-prolinamide with an appropriate oxidizing agent to provide N-$K_2$-protected-N-methyl-D-phenylalanyl-N-[1-[3-[[bis[($K_1$-protected)amino]methylene]-amino]propyl]-3,3-difluoro-2-oxohexyl]-L-prolinamide; and (d) deprotecting N-$K_2$-protected-N-methyl-D-phenylalanyl-N-[1-[3-[[bis[($K_1$-protected)amino] methylene]amino]propyl]-3,3-difluoro-2-oxohexyl]-L-prolinamide with a suitable deprotecting agent to provide N-methyl-D-phenylalanyl-N-[1-[3-[(aminoiminomethyl)amino]propyl]-3,3-difluoro-2-oxohexyl]-L-prolinamide or a pharmaceutically acceptable salt thereof.

2. A process according to claim 1 wherein the guanylating agent is added in a ratio of about 0.9 to about 1.2 molar equivalents per 1.0 molar equivalent of 9,6-diamino-5-hydroxy-4,4-difluorononane, or a pharmaceutically acceptable salt thereof.

3. A process according to claim 1 wherein the guanylating agent is added in a ratio of about 0.95 to about 1.05 molar equivalents per 1.0 molar equivalent of 9,6-diamino-5-hydroxy-4,4-difluorononane, or a pharmaceutically acceptable salt thereof.

4. A process according to claim 1 wherein $K_1$ is tert-butyloxycarbonyl.

5. A process according to claim 4 wherein $K_2$ is tert-butyloxycarbonyl.

6. A process according to claim 1 wherein the reaction of 9,6-diamino-5-hydroxy-4,4-difluorononane, or a pharmaceutically acceptable salt thereof, with an appropriate guanylating agent is carried out at a temperature of from about −30° C. to about 20° C.

7. A process according to claim 1 wherein the reaction of 9,6-diamino-5-hydroxy-4,4-difluorononane, or a pharmaceutically acceptable salt thereof, with an appropriate guanylating agent is carried out at a temperature of from about −15° C. to about 5° C.

8. A process according to claim 2 wherein the appropriate guanylating agent is bis-Boc-amidinopyrazole or bis-Boc-S-methylisothiourea.

9. A process according to claim 3 wherein the appropriate guanylating agent is bis-Boc-amidinopyrazole or bis-Boc-S-methylisothiourea.

10. A process according to claim 8 wherein the reaction of 9,6-diamino-5-hydroxy-4,4-difluorononane, or a pharmaceutically acceptable salt thereof, with an appropriate guanylating agent is carried out at a temperature of from about −15° C. to about 5° C.

11. A process according to claim 10 wherein the appropriate oxidizing agent is a dimethyl sulfide complex under Swern conditions.

12. A process for preparing N-9-[1-[3-[bis($K_1$-protected) amino]methylene]amino]-6-amino-5-hydroxy-4,4-difluorononane comprising reacting 9,6-diamino-5-hydroxy-4,4-difluorononane, or a pharmaceutically acceptable salt thereof, with an appropriate guanylating agent to give N-9-[1-[3-[bis($K_1$-protected)amino] methylene]-amino]-6-amino-5-hydroxy-4,4-difluorononane, wherein $K_1$ is an N-protecting group suitable for protecting the nitrogens of guanyl moieties.

13. A process according to claim 12 wherein the guanylating agent is added in a ratio of about 0.9 to about 1.2 molar equivalents per 1.0 molar equivalent of 9,6-diamino-5-hydroxy-4,4-difluorononane, or a pharmaceutically acceptable salt thereof.

14. A process according to claim 12 wherein the guanylating agent is added in a ratio of about 0.95 to about 1.05 molar equivalents per 1.0 molar equivalent of 9,6-diamino-5-hydroxy-4,4-difluorononane, or a pharmaceutically acceptable salt thereof.

15. A process according to claim 12 wherein the reaction of 9,6-diamino-5-hydroxy-4,4-difluorononane, or a pharmaceutically acceptable salt thereof, with an appropriate guanylating agent is carried out at a temperature of from about −30° C. to about 20° C.

16. A process according to claim 12 wherein the reaction of 9,6-diamino-5-hydroxy-4,4-difluorononane, or a pharmaceutically acceptable salt thereof, with an appropriate guanylating agent is carried out at a temperature of from about −15° C. to about 5° C.

17. A process according to claim 13 wherein the appropriate guanylating agent is bis-Boc-amidinopyrazole or bis-Boc-S-methylisothiourea.

18. A process according to claim 14 wherein the appropriate guanylating agent is bis-Boc-amidinopyrazole or bis-Boc-S-methylisothiourea.

19. A process according to claim 17 wherein the reaction of 9,6-diamino-5-hydroxy-4,4-difluorononane, bis-hydrochloride with an appropriate guanylating agent is carried out at a temperature of from about −15° C. to about 5° C.

20. A process according to claim 12 wherein $K_1$ is tert-butyloxycarbonyl.

* * * * *

UNITED STATES PATENT AND TRADEMARK OFFICE
CERTIFICATE OF CORRECTION

PATENT NO. : 5,739,354

DATED : April 14, 1998

INVENTOR(s) : Duane E. Rudisill

It is certified that error appears in the above-identified patent and that said Letters Patent is hereby corrected as shown below:

Column 2, Line 5 Patent reads " there exist difficulties" and should read -- there exists difficulties -- .

Column 10, Line 25 Patent reads " $N^\delta$- benzlocarbonyl " and should read -- $N^\delta$- benzyloxycarbonyl --.

Column 10, Line 34, "0.5 to 1 hours" should read --0.5 to 1 hour--

Column 13, Line 5 Patent reads "siiued" and should read -- issued -- .

Column 16, Line 44 Patent reads "dicyloherylurea" and should read --dicylohexylurea -- .

Column 18, Line 11 Patent reads "(dr, " and should read -- (dt, --.

Column 19, Line 22 Patent reads "$K_1$ = Box" and should read -- $K_1$ = Boc --

Column 19, Line 23 Patent reads "$K_1$ = Boc" and should read -- $K_2$ = Boc -- .

Abstract Patent reads "preparing preparing " and should read -- preparing -- .

Signed and Sealed this

Eighteenth Day of April, 2000

*Attest:*

Q. TODD DICKINSON

*Attesting Officer*        *Director of Patents and Trademarks*